(12) United States Patent
Matsui

(10) Patent No.: US 10,525,209 B2
(45) Date of Patent: Jan. 7, 2020

(54) NEEDLE-EQUIPPED SYRINGE AND INJECTION MOLDING DIE FOR THE SAME

(71) Applicant: TERUMO KABUSHIKI KAISHA, Tokyo (JP)

(72) Inventor: Takayuki Matsui, Shizuoka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 677 days.

(21) Appl. No.: 15/074,721

(22) Filed: Mar. 18, 2016

(65) Prior Publication Data

US 2016/0199591 A1 Jul. 14, 2016

Related U.S. Application Data

(63) Continuation of application No. PCT/JP2013/075321, filed on Sep. 19, 2013.

(51) Int. Cl.
*A61M 5/34* (2006.01)
*B29C 45/36* (2006.01)
(Continued)

(52) U.S. Cl.
CPC ............. *A61M 5/343* (2013.01); *B29C 45/03* (2013.01); *B29C 45/261* (2013.01); *B29C 45/36* (2013.01);
(Continued)

(58) Field of Classification Search
CPC ............... A61M 5/343; A61M 5/3129; B29C 2045/363; B29C 2045/0027; B29C 45/03;
(Continued)

(56) References Cited

U.S. PATENT DOCUMENTS 6,494,866 B1 * 12/2002 Robinson ........... A61M 5/31511
604/228
2004/0169318 A1 * 9/2004 Chiba ................... B29C 45/261
264/328.1
(Continued)

FOREIGN PATENT DOCUMENTS

JP   H07-178171 A   7/1995
JP   2004-050444 A   2/2004
(Continued)

OTHER PUBLICATIONS

International Search Report for PCT/JP2013/075321 dated Oct. 22, 2013.

*Primary Examiner* — Imani N Hayman
*Assistant Examiner* — Tiffany Legette
(74) *Attorney, Agent, or Firm* — Foley & Lardner LLP

(57) ABSTRACT

A needle-equipped syringe reduces an inclination of a needle by reducing an inclination of a core pin when insert molding is performed. The needle-equipped syringe includes a barrel formed using a resin and having a cylindrical body, a nozzle part provided at a distal end of the body, and an opening part provided at a proximal end of the body; and an injection needle held by the nozzle part. The injection needle and the barrel are integrally molded so that an axis of the injection needle is substantially parallel to an axis of the body. The body has a thick part and a thin part located at a proximal end of the body at opposing positions across the axis of the body. At the proximal end of the body, an axis of an inner surface of the body is offset from an axis of an outer surface of the body.

6 Claims, 5 Drawing Sheets

(51) Int. Cl.
  *B29C 45/26* (2006.01)
  *B29C 45/03* (2006.01)
  *B29K 101/12* (2006.01)
  *B29K 105/20* (2006.01)
  *B29K 705/00* (2006.01)
  *B29L 31/00* (2006.01)

(52) U.S. Cl.
  CPC ..... *A61M 2207/00* (2013.01); *A61M 2207/10* (2013.01); *B29C 2045/363* (2013.01); *B29K 2101/12* (2013.01); *B29K 2105/20* (2013.01); *B29K 2705/00* (2013.01); *B29L 2031/7544* (2013.01)

(58) Field of Classification Search
  CPC ............. B29C 45/14065; B29C 45/261; B29L 2031/7544
  See application file for complete search history.

(56) References Cited

U.S. PATENT DOCUMENTS

| | | | |
|---|---|---|---|
| 2008/0195059 A1 | 8/2008 | Sudo et al. | |
| 2010/0174236 A1* | 7/2010 | Burns | A61M 5/3202 604/110 |
| 2013/0138047 A1 | 5/2013 | Takemoto et al. | |

FOREIGN PATENT DOCUMENTS

| | | |
|---|---|---|
| JP | 2008-194317 A | 8/2008 |
| JP | 2013-070892 A | 4/2013 |
| WO | WO-2012/043544 A1 | 4/2012 |

* cited by examiner

NEEDLE-EQUIPPED SYRINGE AND INJECTION MOLDING DIE FOR THE SAME

CROSS-REFERENCE TO RELATED APPLICATIONS

This application is a continuation application filed under 35 U.S.C. § 111(a) claiming the benefit under 35 U.S.C. §§ 120 and 365(c) of PCT International Application No. PCT/JP2013/075321, filed on Sep. 19, 2013. The contents of this application are hereby incorporated by reference their entirety.

BACKGROUND

The present disclosure relates to a needle-equipped syringe in which an injection needle is provided and fixed to a nozzle part of a barrel, an injection molding die for the same, and a manufacturing method for the needle-equipped syringe.

An injector includes a barrel having a cylinder configured to be filled with medicine, a plunger inserted into the cylinder, and an injection needle provided at a distal end of the cylinder. As a syringe utilizing the injector, a needle-equipped syringe is used other than the one in which a needle base with the injection needle is mounted at the time of usage. The needle-equipped syringe has the barrel to which the needle has been previously attached, and a process for mounting the injection needle at the time of the usage can be omitted. Therefore, the needle-equipped syringe can contribute to improve an efficiency and safety of a medical practice.

The needle-equipped syringe is manufactured by previously manufacturing the barrel, inserting the injection needle through a through hole opened in the barrel, and bonding the injection needle and the barrel to each other. However, in the needle-equipped syringe, since the injection needle is fixed to the barrel with an adhesive, a unit price is increased due to an increase in material costs and manufacturing processes. Also, when the barrel has been filled with the medicine, there is a possibility that the medicine has contact with the adhesive.

WO 2012/043544 A describes a needle-equipped syringe manufactured by insert molding performed by injecting the resin into the injection molding die in which the injection needle is placed. The injection needle is directly provided and fixed to the nozzle part of the barrel. Accordingly, the problems described in WO 2012/043544 A can be solved.

SUMMARY

However, when the insert molding is performed by using the injection molding die, a pressure and a speed of the resin injected into a cavity space may be non-uniform around a core pin that is inserted to form a hollow part of the barrel configured to be filled with the medicine, at the time when the resin is injected from the resin injection gate to the cavity space of the die. Accordingly, the core pin is inclined in the cavity space, and the axis of the injection needle supported by the core pin is excessively inclined with respect to the axis of the core pin. A defective product is easily made in which the axis of the injection needle is excessively inclined with respect to an axis of an outer peripheral surface of the body of the barrel in the needle-equipped syringe which is a molded article.

When the injection needle is excessively inclined, it is difficult to stick on a cap to protect the injection needle straight after the needle-equipped syringe has been manufactured. Therefore, manufacturing efficiency gets worse. Also, it is difficult to attach the cap to the injection needle so that it does not fall out. As a result, when high pressure sterilization treatment is performed on the molded needle-equipped syringe and when the molded needle-equipped syringe is transported to a medical institution, there is a possibility that the cap may unexpectedly detach. Also, when the needle punctures a surface of a body for a hypodermic injection, an intradermal injection, an intravenous injection, an intramuscular injection, or the like, it is necessary to adjust the orientation of the syringe according to the excessive inclination of the injection needle in a case where the axis of the injection needle held by the barrel for each needle-equipped syringe is excessively shifted from the axis of the outer peripheral surface of the body of the barrel. As a result, the efficiency of the medical procedure deteriorates. Therefore, it is necessary to reduce the inclination of the injection needle generated when the needle-equipped syringe is manufactured by the insert molding.

An object of certain embodiments of the present invention is to provide a needle-equipped syringe that reduces an inclination of an injection needle by reducing an inclination of a core pin when insert molding is performed, an injection molding die for molding the same, and a manufacturing method for the needle-equipped syringe.

A needle-equipped syringe includes a barrel formed using a resin and having a cylindrical body, a nozzle part provided at a distal end of the body, and an opening part provided at a proximal end of the body; and an injection needle configured to be held by the nozzle part. The injection needle and the barrel are integrally molded so that an axis of the injection needle is substantially parallel to an axis of the body. The body has a thick part and a thin part, which are located at a proximal end of the body at positions opposed to each other across the axis of the body. At the proximal end of the body, an axis of an inner peripheral surface of the body is eccentric (i.e., offset) from an axis of an outer surface of the body.

A single gate mark generated at the time of molding the barrel may be provided on the opening part or an outer surface of the body in the barrel, and the thin part may be provided at a side of the gate mark in a circumferential direction of the body.

The opening part may include a flange extending perpendicularly to the axis of the body and extending outwardly. The single gate mark may be provided on an outer surface of the flange.

A length from a distal end of the body to a proximal end of the body in an axis direction of the body may be four to twelve times an internal diameter of the proximal end of the body.

A difference between a thickness of the thick part and a thickness of the thin part may be 50 to 500 μm.

An inclination of the axis of the injection needle with respect to the axis of the body may be equal to or less than 2°.

An injection molding die for molding a needle-equipped syringe that includes a barrel formed using a resin and having a cylindrical body, a nozzle part provided at the distal end of the body, and an opening part provided at a proximal end of the body; and an injection needle held by the nozzle part, and in which the injection needle and the barrel are integrally molded so that an axis of the injection needle is substantially parallel to an axis of the body, is provided. The injection molding die includes a female die having a recessed part for molding an outer surface of the barrel, and a holding part for holding a distal side of the injection needle; a male die having a core pin for molding an inner surface of the barrel, and a holding hole for holding a proximal end of the injection needle distal to the core pin; and a resin injection gate configured to inject the resin into a cavity space formed by the recessed part and the core pin inserted into the recessed part so that the holding hole is positioned in the recessed part. The core pin is inserted into the recessed part so as to be offset with respect to an axis of the recessed part.

The resin injection gate may be formed as a single part configured to mold the outer surface of the body or a part configured to mold the outer surface of the opening part. The core pin may be inserted into the recessed part so as to be eccentric (i.e., offset) to the side of the resin injection gate with respect to the axis of the recessed part.

The resin injection gate may be formed as a single part configured to mold an outer surface of a flange extending in the opening part.

A length of the core pin in an axis direction of the core pin may be four to twelve times a diameter of the core pin.

The injection molding die may be a hot runner die that includes a heater for heating a runner which reaches the resin injection gate.

The holding part may hold a part of the injection needle distal to a part of the injection needle held by the nozzle part.

A method of manufacturing a needle-equipped syringe using an injection molding die, the needle-equipped syringe including a barrel formed using a resin and having a cylindrical body, a nozzle part provided at a distal end of the body, and an opening part provided at a proximal end of the body; and an injection needle held by the nozzle part, and in which the injection needle and the barrel are integrally molded so that an axis of the injection needle is substantially parallel to an axis of the body, and the injection molding die including a female die having a recessed part for molding an outer surface of the barrel, and a holding part for holding a distal side of the injection needle; a male die having a core pin for molding an inner surface of the barrel, and a holding hole for holding a proximal end of the injection needle distal to the core pin; and a resin injection gate configured to inject the resin into a cavity space formed by the recessed part and the core pin inserted into the recessed part so that the holding hole is positioned in the recessed part, the method including inserting the core pin into the recessed part as being eccentric with respect to an axis of the recessed part in a direction in which an axis of an injection needle is inclined with respect to an axis of a body, in a case where the barrel is molded by injecting the resin from the resin injection gate into the cavity space in a state where the core pin is inserted into the recessed part so that an axis of the core pin substantially coincides with the axis of the recessed part, the holding hole holds the proximal end of the injection needle, and the holding part holds the distal side of the injection needle; and molding the barrel by injecting the resin from the resin injection gate into the cavity space in a state where the holding hole holds of the proximal end of the injection needle and the holding part holds the distal side of the injection needle.

The core pin may be inserted into the recessed part as being eccentric (i.e., offset) with respect to the axis of the recessed part so that the pressure and/or the speed of the resin injected into the cavity space becomes substantially uniform around the core pin in a cross section perpendicular to the axis of the core pin.

The resin injection gate is formed as a single part configured to mold the outer surface of the body or a part configured to mold the outer surface of the opening part, and the core pin may be inserted into the recessed part as being eccentric (i.e., offset) to the side of the resin injection gate with respect to the axis of the recessed part.

The barrel may be molded by injecting the resin into the cavity space from the resin injection gate which is formed as a single in a part configured to mold the outer surface of a flange of the opening part.

The holding part may hold the needle by a part of the needle distal to the nozzle part.

The injection molding die may be a hot runner die that includes a heater for heating a runner which reaches the resin injection gate, and when the molded needle-equipped syringe is taken out from the injection molding die, the runner may be heated by the heater, and the needle-equipped syringe may be separated from the runner.

The needle-equipped syringe according to the present invention is molded so as to include a thick part and a thin part at positions opposed to each other across the axis of the body of the barrel in the proximal end part of the body. Therefore, the axis of the injection needle held by the nozzle part is substantially parallel to the axis of the body, and the inclination of the injection needle is reduced as much as possible. Accordingly, an efficiency of a medical practice such as puncture can be improved. Since the axis of the injection needle is substantially parallel to the axis of the body in the needle-equipped syringe, flow lines of the body of the syringe and the injection needle to a punctured part substantially coincide with each other, and the injection needle can be punctured in an intended direction. Therefore, a medical accident can be prevented such as those in which flow lines of the syringe and the injection needle do not coincide and the injection needle incorrectly punctures a part which is not desired. Accordingly, the needle-equipped syringe can be safely used. In addition, regarding the needle-equipped syringe, the number of defective products in which the axis of the injection needle is different from the axis of the outer peripheral surface of the body is reduced. Also, the needle-equipped syringe has improved yield and high reliability.

According to the injection molding die of the needle-equipped syringe according to certain embodiments of the present invention, the pressure and the speed of the resin can be adjusted to be substantially uniform around the core pin in the axis direction of the core pin when the resin is injected into the cavity space. According to this, since the inclination of the core pin can be reduced as much as possible, the injection molding die can be used to accurately manufacture the needle-equipped syringe in which the axis of the injection needle is substantially parallel to the axis of the outer peripheral surface of the body.

According to the manufacturing method for the needle-equipped syringe according to certain embodiments of the present invention, the pressure and the speed of the resin injected into the cavity space are adjusted so as to be substantially uniform around the core pin in the axis direction of the core pin by inserting the core pin into the recessed part as offset with respect to the axis of the recessed part. Then, the needle-equipped syringe in which the axis of the injection needle is substantially parallel to the axis of the outer peripheral surface of the body can be accurately manufactured. Accordingly, the inclination of the core pin can be reduced as much as possible, and the needle-equipped syringe in which the axis of the injection needle is substantially parallel to the axis of the outer peripheral surface of the body can be accurately manufactures. According to the manufacturing method, an efficiency of a process for molding the needle-equipped syringe can be improved.

DETAILED DESCRIPTION

Embodiments according to the present invention will be described in detail below. However, the range of the present invention is not limited to these embodiments.

Figure 1:
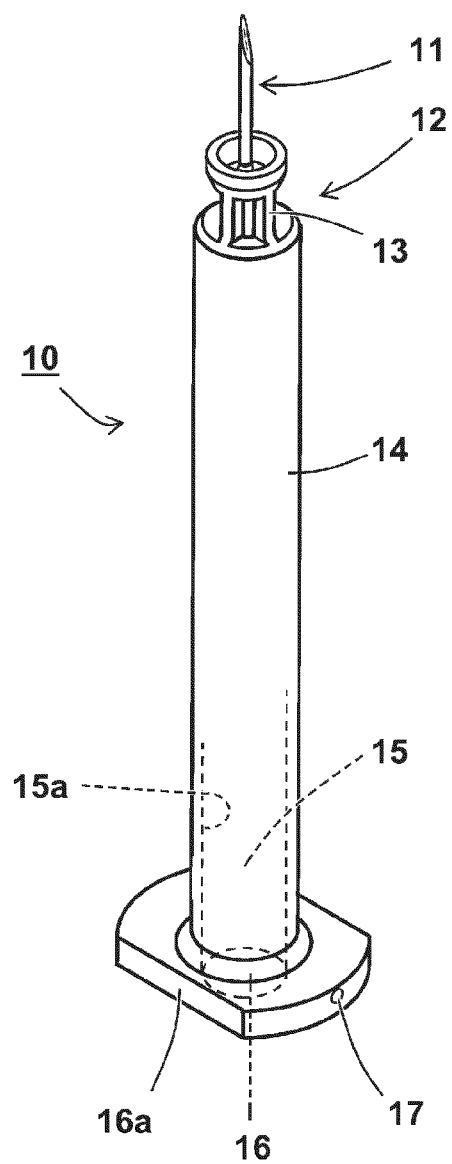
FIG. 1 is a perspective view of one embodiment of a needle-equipped syringe.

One embodiment of a needle-equipped syringe 10 will be described below with reference to FIGS. 1 to 3. As illustrated in FIG. 1, the needle-equipped syringe 10 is formed of a barrel 12 and an injection needle 11. The barrel 12 is formed of resin, and the injection needle 11 is formed of a metal needle tube, which is integrally joined with a nozzle part 13.

The barrel 12 has a cylindrical shape and includes a hollow part 15 configured to be filled with medicine. The barrel 12 includes the nozzle part 13 provided at a distal end, a body 14 which is continuously arranged around the nozzle part 13 and forms a peripheral wall 15a extending toward a proximal end, and an opening part 16 provided at the proximal end. The opening part 16 has a flange 16a that extends perpendicularly to the axis of the body 14 and extends outward. An outer surface of the flange 16a has a single gate mark 17, which is formed by a resin injection gate 28 (refer to FIG. 2) when the needle-equipped syringe 10 is molded.

Figure 3:
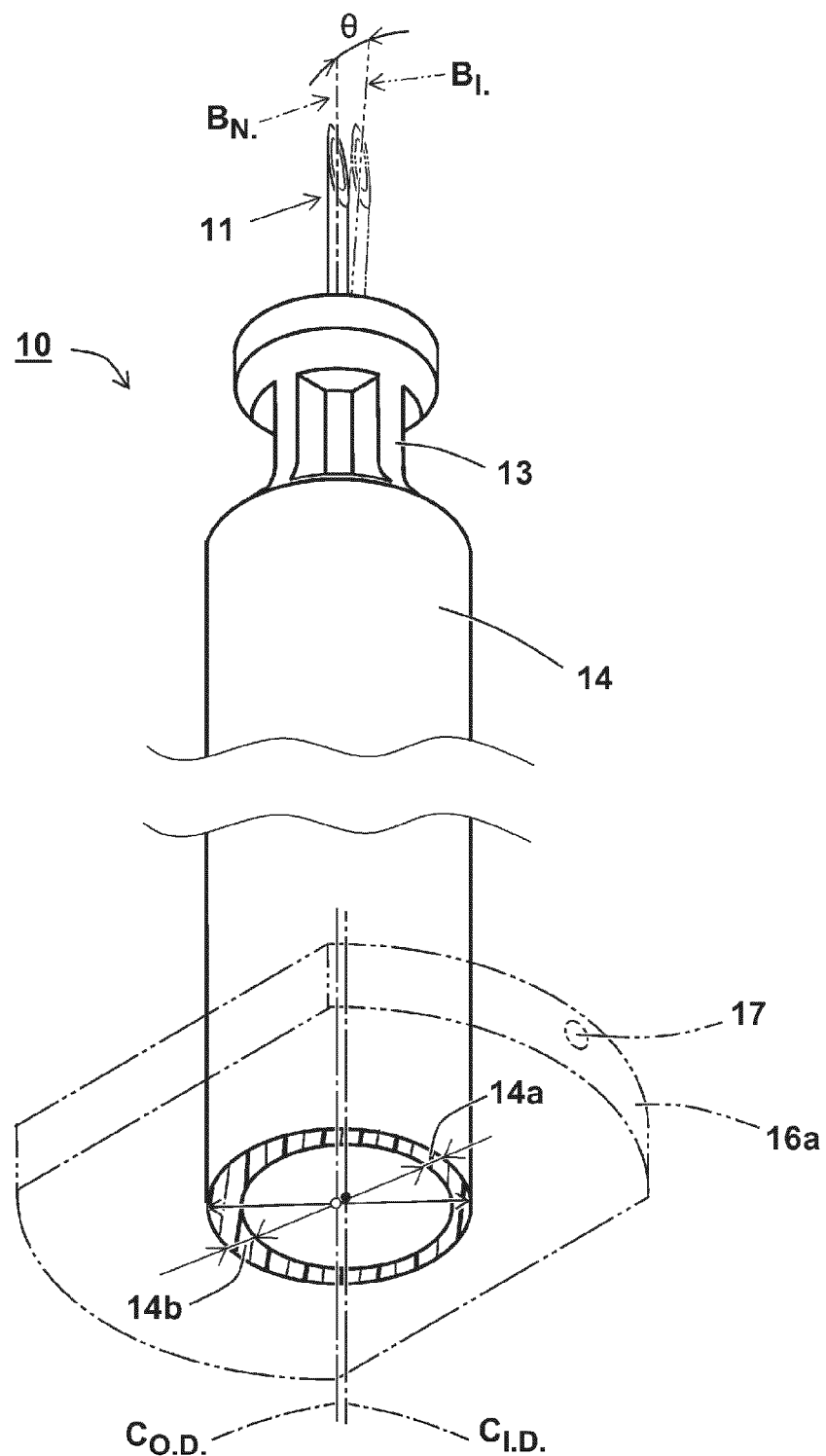
FIG. 3 is a perspective view of a main part of the needle-equipped syringe according to an embodiment of the present invention.

As illustrated in FIG. 3, the peripheral wall 15a is formed at the proximal end of the body 14 in a state where an axis $C_{I.D.}$ of the inner peripheral surface of the body 14 is eccentric (i.e., offset) to the side of the gate mark 17 with respect to an axis $C_{O.D.}$ of the outer peripheral surface of the body 14. Accordingly, a thin part 14a is formed on the side of the gate mark 17 of the body 14. A thick part 14b is formed at a position opposite to the thin part 14a across the axis $C_{O.D.}$ of the outer peripheral surface of the body 14 and the axis $C_{I.D.}$ of the inner peripheral surface. In the circumferential direction of the body 14, the thickness of the peripheral wall 15a is gradually increased from the thin part 14a to the thick part 14b.

A difference between a thickness of the thin part 14a and a thickness of the thick part 14b is of 50 to 500 µm, preferably, 50 to 150 µm, and more preferably, 80 to 120 µm. As long as the axis of the injection needle 11 is substantially parallel to the axis of the outer peripheral surface of the body 14 and the injection needle 11 is hardly inclined (by reducing the inclination of the injection needle 11 as much as possible), the material thicknesses of the thin part 14a and the thick part 14b may be equal to each other to the side of the nozzle part 13 in the axis direction of the body 14, and may be gradually changed. When the material thickness of the thin part 14a is gradually increased to the side of the nozzle part 13 in the axis direction of the body 14, the material thickness of the thick part 14b is gradually reduced to the side of the nozzle part 13 in the axis direction of the body 14. On the other hand, when the material thickness of the thick part 14b is gradually increased to the side of the nozzle part 13 in the axis direction of the body 14, the material thickness of the thin part 14a is gradually reduced to the side of the nozzle part 13 in the axis direction of the body 14. When the thin part 14a is positioned on the side of the gate mark 17, the peripheral wall 15a includes the gate mark 17 and the axis of the body 14, and the peripheral wall 15a is arranged plane symmetrically while having the cross section parallel to the axis of the body 14 as a symmetry plane.

The nozzle part 13 is formed in the direction perpendicular to the axis direction of the outer peripheral surface of the body 14 so as to have the proximal end part of the nozzle part 13 as a cruciform cross section and have a circular distal end part of the nozzle part 13. The injection needle 11 passes through the center of the circle, and the circular distal end part around the injection needle 11 is swollen. The distal end part of the nozzle part 13 may have a dome shape, a conical shape, and a columnar shape. A diameter of the proximal end part of the nozzle part 13 may be the same as that of the distal end part. Also, when the strength of the nozzle part 13 to hold the injection needle 11 can be secured, the shape of the proximal end part of the nozzle part 13 may be a polygonal shape such as a square pillar and a hexagonal pillar or a column.

The injection needle 11 passes through the nozzle part 13, and the proximal end part of the injection needle 11 is slightly projected toward the hollow part 15 of the body 14. A region from the center part of the injection needle 11 to a tip part of the distal end is held in a state where the region is projected from the nozzle part 13 to the side of the distal end. As illustrated in FIG. 3, it is preferable that the axis of the held injection needle 11 be not inclined at all or be hardly inclined so as to be substantially parallel to the axis of the outer peripheral surface of the body 14. Substantially parallel means that the axis of the injection needle 11 is completely parallel to the axis $C_{O.D.}$ of the outer peripheral surface of the body 14 of the barrel 12 (injection needle 11 indicated by solid line) or that the inclination of the axis of the injection needle 11 (injection needle 11 indicated by double-dashed line) with respect to the axis $C_{O.D.}$ of the outer peripheral surface of the body 14 is equal to or less than 2°. Even when the injection needle 11 is slightly inclined from the axis of the barrel 12 to the radial direction of the body 14 (refer to axis $B_I$ in FIG. 3), it is preferable that the inclination θ of the axis $B_I$ of the inclined injection needle 11 with respect to the axis $B_n$ of the ideal injection needle 11, which is not inclined, be 5° at the maximum. It is more preferable that the inclination θ be less than 4°, even more preferable that the inclination θ be less than 3°, and still more preferable that the inclination θ be less than 2°. It is further more preferable that the inclination θ be less than 1°. It is most preferable that the inclination θ be 0°.

It is not necessary that the position where the needle proximal end part of the injection needle 11 is held by the nozzle part 13 is at the center of the nozzle part 13 so as to be on the axis $C_{I.D.}$ of the inner peripheral surface of the body 14 of the barrel 12 or on the axis $C_{O.D.}$ of the outer peripheral surface, and the position of the needle proximal end part may be shifted with respect to the body 14 in the radial direction. When the amount of the medicine contained in the needle-equipped syringe 10 is large, a puncture angle with respect to the surface of the body can be reduced by shifting the position of the needle proximal end part to the side of the outer peripheral surface of the body 14 in the radial directions of these axes. This is effective because the injection can be smoothly given to blood vessels, muscles, and under the skin.

The resin forming the barrel 12 is selected from the viewpoint of a chemical resistance, a heat resistance, gas and bacteria barrier properties, safety for a living body, transparency, and the like. For example, thermoplastic resin exemplified as polyolefin resin such as polyethylene, polypropylene, and cycloolefin polymer, polystyrene, polycarbonate, polyester such as polyester terephthalate, and polyamide is used. Especially, it is preferable to use cyclic olefin homopolymer or cyclic olefin copolymer. These resins are transparent so that the chemical stored therein can be visually confirmed from outside and have a small interaction with the chemical.

The material of the injection needle 11 is a material which can be formed by insert molding and selected from the viewpoint of a chemical resistance, a heat resistance, gas and bacteria barrier properties, safety for a living body, and the like. For example, stainless and nickel-free stainless can be used as the material of the injection needle 11. However, inexpensive stainless which can be relatively easily molded is preferable.

Figure 2:
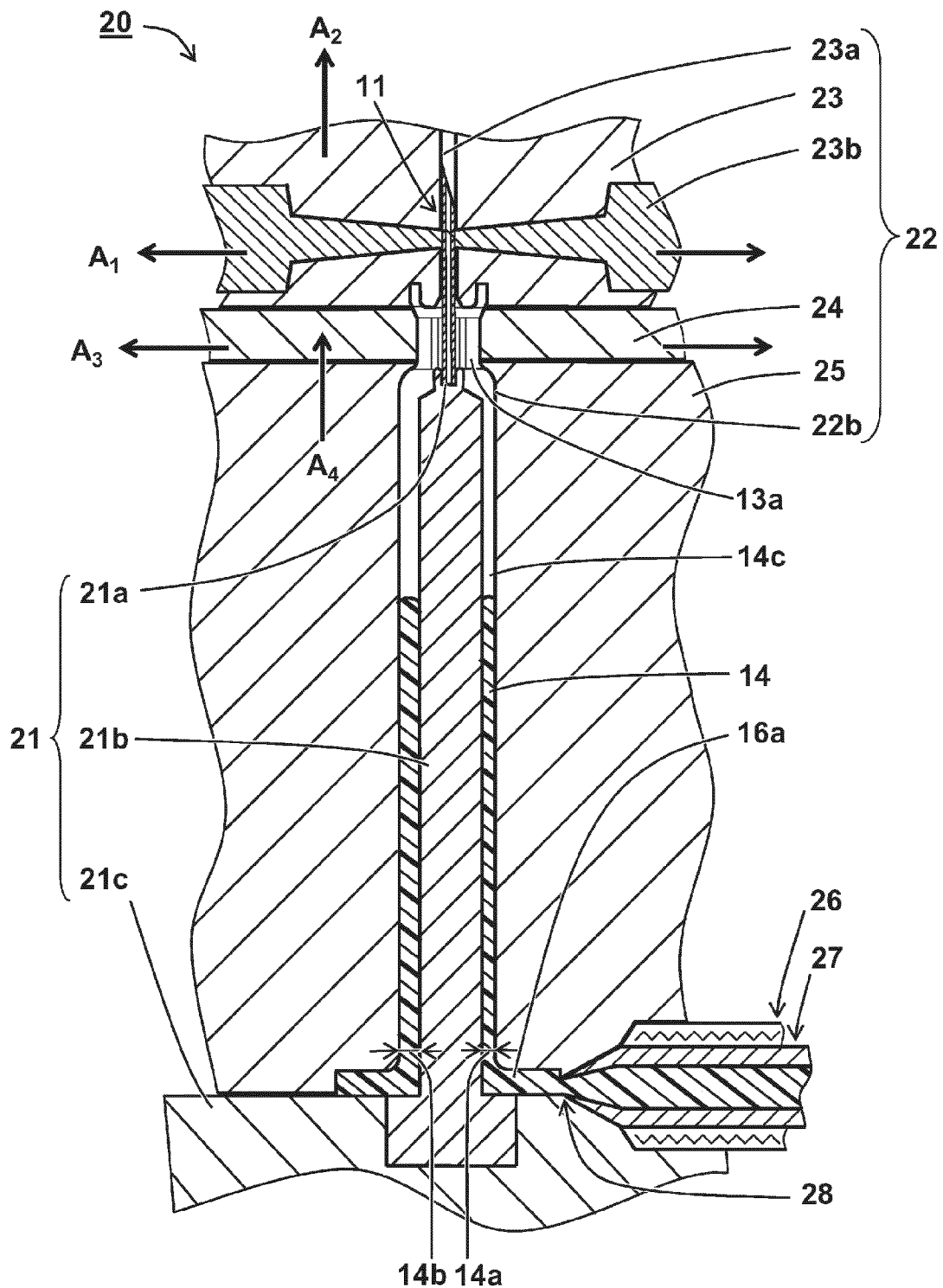
FIG. 2 is a schematic cross-sectional diagram of a state where resin is injected into an injection molding die when the needle-equipped syringe according to an embodiment of the present invention is manufactured.

As illustrated in FIG. 2, the needle-equipped syringe 10 formed in this way is molded by using an injection molding die 20. The injection molding die 20 includes a male die 21 and a female die 22.

The male die 21 is formed of a core pin 21*b* which molds the inner surface of the barrel 12, a holding hole 21*a* which is formed at the distal end of the core pin 21*b*, and a fitting plate 21*c* to which the proximal end of the core pin 21*b* is fitted. A supporting plate for supporting a proximal end surface of the body forming female die 25 may be provided between the body forming female die 25 and the fitting plate 21*c*. In this case, the core pin 21*b* extends through the supporting plate, and the proximal end of the core pin 21*b* is fitted into the fitting plate 21*c*.

The core pin 21*b* has a columnar shape of which the diameter is uniform and a substantially columnar shape or a conical shape of which the diameter gradually changes upward. The distal end part is formed in a substantially conical shape or a hemispherical shape, and more preferably, in a substantially conical shape.

The holding hole 21*a* is formed at the center of the distal end of a cylindrical part projected from the distal end part of the core pin 21*b* which has a substantially conical shape and holds a needle proximal end part of the injection needle 11. Since the proximal end part of the injection needle 11 is covered and closed with the holding hole 21*a*, resin can be prevented from entering a needle hole of the injection needle 11 when the resin is injected.

The proximal end of the core pin 21*b* is fitted into the hole of the fitting plate 21*c* and is screwed into the hole so as not to be separated.

The female die 22 includes the body forming female die 25, a nozzle part forming female die 24, and a needle holding female die 23. The female die 22 is formed by placing the body forming female die 25 on the fitting plate 21*c*, placing the nozzle part forming female die 24 at upper end of the body forming female die 25, and placing the needle holding female die 23 at the upper end of the nozzle part forming female die 24.

A hole to form a cavity space between the core pin 21*b* and the body forming female die 25 passes through the body forming female die 25.

The nozzle part forming female die 24 includes a pair of dies opposed to each other to be freely opened in the direction perpendicular to the axis direction of the core pin 21*b*. On the surfaces of the pair of dies 24 opposed to each other, depressions to form the nozzle part 13 are formed.

The needle holding female die 23 includes a depression to form a circular distal end part of the nozzle part 13 on a lower surface on the side of the nozzle part forming female die 24 and a storing hole 23*a* to store the injection needle 11. A holding part 23*b* to hold the injection needle 11 is provided above the depression.

The holding part 23*b* removably penetrates the needle holding female die 23 in the direction perpendicular to the axis direction of the injection needle 11 so as to fix the injection needle 11 in the axis direction.

The female die 22 includes a recessed part 22*b* which is formed of a hole of the body forming female die 25, the depression of the nozzle part forming female die 24, and the depression of the needle holding female die 23 to form the cavity space. The recessed part 22*b* molds an outside surface of the barrel 12 by closing the nozzle part forming female die 24 on the body forming female die 25 and placing the needle holding female die 23 there.

The core pin 21*b* is inserted into the recessed part 22*b* so that the holding hole 21*a* is positioned in the recessed part 22*b*. The cavity space is formed between the recessed part 22*b* of the female die 22 and the male die 21, which inserts the core pin 21*b* into the recessed part 22*b*. The cavity space forms a gap to form the body 14, the nozzle part 13, and the flange 16*a* of the barrel 12 between the recessed part 22*b* and the core pin 21*b*. The core pin 21*b* is arranged so as to be eccentric (i.e., offset) to the side of the resin injection gate 28 with respect to the axis of the recessed part 22*b* in the cavity space. The holding part 23*b* is arranged so as to hold a side of the injection needle 11 distal to the cavity space 13*a* in which the nozzle part 13 is filled with the resin.

The single resin injection gate 28 is provided in the body forming female die 25 to inject the resin into the cavity space. In addition, a tubular runner 27 is provided so that the resin reaches the resin injection gate 28. According to this, the runner 27 communicates with the cavity space for forming the flange 16*a* so that the cavity space can be filled with the resin via the resin injection gate 28. A heater 26 is provided around the runner 27, and the heater 26 keeps a melted state of the resin flown in the runner 27.

The female die 22 is placed on the male die 21 so that the storing hole 23*a* is arranged immediately above the holding hole 21*a* and the injection needle 11 inserted into the holding hole 21*a*. When the core pin 21*b* is inserted into the recessed part 22*b* of the body forming female die 25, the axis of the core pin 21*b* is eccentric (i.e., offset) to the side of the resin injection gate 28. According to the eccentricity, the thick part 14*b* and the thin part 14*a* are respectively formed at positions opposed to each other across the axis of the body 14.

The needle-equipped syringe 10 is manufactured as follows. The needle proximal end part of the injection needle 11 is inserted into the holding hole 21*a* and is held by and fixed to the male die 21. The core pin 21*b* is inserted into the hole of the body forming female die 25 so that the axis of the core pin 21*b* of the male die 21 is eccentric (i.e., offset) to the side of the resin injection gate 28 with respect to the axis of the recessed part 22b of the body forming female die 25. When the core pin 21b is inserted into the recessed part 22b so that the axis of the core pin 21b coincides with the axis of the recessed part 22b of the female die 22 and the barrel 12 is molded (refer to FIG. 5), the injected resin pushes down the core pin 21b to the opposite side of the resin injection gate 28. As a result, the axis of the injection needle 11 is inclined to the side of the resin injection gate 28 with respect to the axis of the body 14 of the barrel 12. However, when the axis of the core pin 21b is eccentric (i.e., offset) to the side of the resin injection gate 28 with respect to the axis of the hole of the body forming female die 25, the core pin 21b is not pushed down. The direction of the inclination of the core pin 21b is different according to the position and the number of resin injection gates 28 and the flow of the resin in the cavity space. Therefore, the inclination of the axis of the injection needle 11 with respect to the axis of the body 14 of the barrel 12 is similarly different. Therefore, the core pin 21b is inserted into the recessed part 22b of the female die 22, the needle proximal end part of the injection needle 11 is held by the holding hole 21a of the core pin 21b and the part on the side of the needle distal end than the needle proximal end part of the injection needle 11 is held by the holding part 23b of the female die 22 so that the axis of the core pin 21b substantially corresponds to the axis of the recessed part 22b of the female die 22. In this state, when the barrel 12 is molded by injecting the resin from the resin injection gate 28 into the cavity space, the axis of the injection needle 11 is inclined with respect to the axis of the body 14 of the barrel 12. The core pin 21b is eccentric (i.e., offset) with respect to the axis of the recessed part 22b of the female die 22 in the inclining direction and is inserted into the recessed part 22b of the female die 22. Accordingly, the inclination of the core pin 21b is reduced, and the inclination of the axis of the injection needle 11 with respect to the axis of the body 14 of the barrel 12 can be reduced.

Subsequently, the pair of the nozzle part forming female dies 24 is moved in an opposite direction of an opening direction $A_3$ and brought into contact with each other, and thereby the recessed part 22b is formed. The needle holding female die 23 is moved to the opposite direction of an opening direction $A_2$ and is placed on the nozzle part forming female die 24 so that the injection needle 11 is inserted into the storing hole 23a of the needle holding female die 23. After that, the holding part 23b is moved to the opposite direction of an opening direction $A_1$. Accordingly, the injection needle 11 is fixed in a state where the axis of the injection needle 11 is substantially parallel to the axis of the core pin 21b. After mold clamping has been performed to the injection molding die 20, the melt resin is injected from the resin injection gate 28 into the cavity space via the runner 27, and insert molding to mold the needle-equipped syringe 10 is performed.

By the insert molding, the cavity space corresponding to the part of the flange 16a, the cavity space 14c corresponding to the part of the body 14, and the cavity space 13a corresponding to the part of the nozzle part 13 are sequentially filled with the resin. When the cavity space is continuously filled with the resin for a while, the resin is filled to the upper end of the cavity space 13a in the injection needle 11 which is held at a fixed position so that the outer periphery of the proximal end part is surrounded by the resin, and the injection needle 11 is held by the barrel 12. The hollow part 15 of the barrel 12 to which the medicine is filled and the opening part 16 through which the medicine is injected into the hollow part 15 are formed by the core pin 21b arranged in the cavity space. An outer wall of the barrel 12 is formed by the recessed part 22b of the cavity space. The resin is cooled and solidified in the injection molding die 20. After that, the holding part 23b is moved to the opening direction $A_1$, and the needle holding female die 23 can be opened. Subsequently, the needle holding female die 23 is moved to the opening direction $A_2$. In addition, the nozzle part forming female die 24 is moved to the opening direction $A_3$. After that, the body forming female die 25 is moved to the opening direction $A_4$, and mold opening is performed to the injection molding die 20. The molded needle-equipped syringe 10 is pulled out and is taken out from the core pin 21b. Burrs generated in the flange 16a due to the resin injection gate 28 are removed as necessary.

The core pin 21b is arranged as being shifted from the center to the side of the resin injection gate 28 in the cavity space. Accordingly, as illustrated in FIG. 3, in the taken-out needle-equipped syringe 10, the axis $C_{I.D.}$ of the inner peripheral surface is eccentric (i.e., offset) to the side of the gate mark 17 with respect to the axis $C_{O.D.}$ of the outer peripheral surface at the proximal end part of the body 14, and the peripheral wall 15a is formed. According to this, the material thickness of a part of the body 14 is reduced on the side of the gate mark 17, and the thin part 14a is formed. Furthermore, the material thickness of a part of the body 14 is increased at the position opposed to the thin part 14a across the axis $C_{O.D.}$ of the outer peripheral surface and the axis $C_{I.D.}$ of the inner peripheral surface, and the thick part 14b is formed. At the time when the barrel 12 is molded by inserting the core pin 21b into the recessed part 22b so that the axis of the core pin 21b substantially coincides with the axis of the recessed part 22b of the female die 22, in a case where the axis of the injection needle 11 is inclined to the direction different from the side of the resin injection gate 28 with respect to the axis of the body 14 of the barrel 12, the barrel 12 is molded by shifting the core pin 21b to the direction in which the injection needle 11 is inclined. According to this, the axis $C_{I.D.}$ of the inner peripheral surface is eccentric to the direction to which the core pin 21b is shifted with respect to the axis $C_{O.D.}$ of the outer peripheral surface at the proximal end part of the body 14, and the peripheral wall 15a is formed. In this case, the material thickness of a part of the body 14 is reduced on the side to which the core pin 21b is shifted, and the thin part 14a is formed. Furthermore, the material thickness of a part of the body 14 is increased at the position opposed to the thin part 14a across the axis $C_{O.D.}$ of the outer peripheral surface and the axis $C_{I.D.}$ of the inner peripheral surface, and the thick part 14b is formed.

The body forming female die 25 configuring the female die 22 of the injection molding die 20 has the resin injection gate 28 on one side. Since the core pin 21b is arranged as being shifted to the direction of the resin injection gate 28 in the cavity space formed by the recessed part 22b of the female die 22 and the male die 21, the pressure and the speed of the resin which is injected into the cavity space 14c can be adjusted so as to be substantially uniform around the core pin 21b in the axis direction of the core pin 21b. Accordingly, the core pin 21b is prevented from being inclined. At the time when the barrel 12 is molded by inserting the core pin 21b into the recessed part 22b so that the axis of the core pin 21b substantially coincides with the axis of the recessed part 22b of the female die 22, in a case where the axis of the injection needle 11 is inclined to the direction different from the side of the resin injection gate 28 with respect to the axis of the body 14 of the barrel 12, the barrel 12 is molded by shifting the core pin 21b to the direction in which the injection needle 11 is inclined. According to this, the pressure and the speed of the resin which is injected into the cavity space 14c can be adjusted so as to be substantially uniform around the core pin 21b in the axis direction of the core pin 21b. Accordingly, the core pin 21b is prevented from being inclined.

Figure 5:
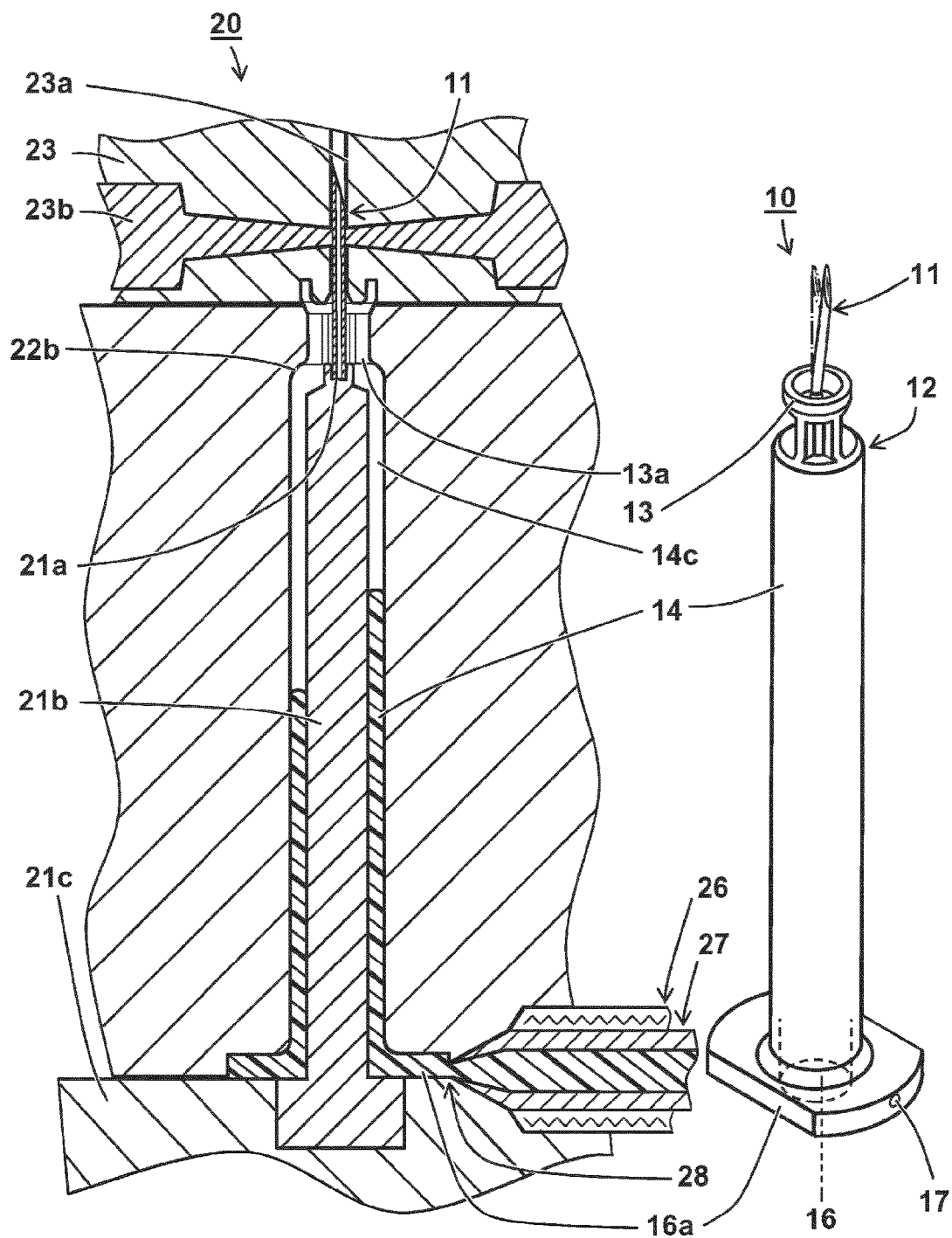
FIG. 5 is a schematic cross-sectional diagram of an injection molding die of a conventional needle-equipped syringe and a perspective view of the needle-equipped syringe molded by using the injection molding die.

When the insert molding is performed by arranging the core pin 21b so that the material thickness of the barrel 12 becomes uniform as is conventionally done, the pressure and the speed of the resin injected to the cavity space 14c on the side of the resin injection gate 28 and the cavity space 14c on the opposite side cannot be adjusted to be equal as illustrated in FIG. 5. The core pin 21b is inclined to the side opposite to the resin injection gate 28. At this time, the needle holding female die 23 holds a part of the injection needle 11 on the side of the needle distal end than a part held by the nozzle part 13. Therefore, a force to prevent the inclination of the injection needle 11 when the core pin 21b is inclined does not act, and the injection needle 11 is easily inclined. Therefore, the injection needle 11 is inclined to a direction opposite to the inclination direction of the core pin 21b. Since the resin is cooled and solidified in this state, the needle-equipped syringe 10 is molded in a state where the injection needle 11 is inclined to the side of the gate mark 17 (refer to the injection needle 11 indicated by a solid line in the exemplary syringe in FIG. 5).

According to the injection molding die 20 of certain embodiments of the present invention, the inclination of the core pin 21b is prevented, and the inclination of the injection needle 11 can be reduced as much as possible (refer to the axis $B_n$ of the injection needle 11 which is not inclined in FIG. 3). The pressure and the speed of the resin which is injected into the cavity space can be maintained to be substantially uniform around the core pin 21b on the side of the resin injection gate 28 and the opposite side in the axis of the core pin 21b. According to this, the resin can be injected into the cavity space without changing the injection speed of the resin, and the resin is filled while maintaining its substantially uniform height around the core pin 21b. As a result, stress for inclining the core pin 21b is not applied, and the inclination of the core pin 21b can be prevented. The inclination of the injection needle 11 can be reduced as much as possible. Even when the injection needle 11 is inclined, an inclination θ of the axis of the inclined injection needle 11 with respect to the axis of the injection needle 11 which is not inclined can be reduced to be equal to or less than 2° (refer to the axis $B_I$ of the inclined injection needle 11 in FIG. 3).

Accordingly, even when the die has a simple structure and can be easily and inexpensively formed, the inclination of the injection needle 11 can be reduced as much as possible. The injection speed of the resin into the cavity space is maintained, and the resin can be quickly injected. Therefore, defective molding such as a flow mark can be prevented. In addition, since the resin can be easily and uniformly injected, an efficiency of the molding process can be improved.

Also, the injection molding die 20 according to certain embodiments of the present invention is a hot runner die having the runner 27 and the heater 26. Therefore, the needle-equipped syringe 10 which is a molded article can be taken out while the resin in the runner 27 is maintained to be in the melted state. As in a case of a cold runner, when the resin is solidified and the product is taken out from the die, it is not necessary to remove the solidified resin in the runner 27 at the same time. Therefore, waste of the resin of the part of the runner 27 is reduced, and a yield can be improved. Especially, when the insert molding is performed to the small needle-equipped syringe 10 of which the maximum amount of filled medicine is one mL, a ratio of the runner with respect to the molded article is relatively large. Therefore, the effect is large. Also, since the process for reducing the resin in the runner 27 is unnecessary, an efficiency for molding the needle-equipped syringe 10 is improved.

The molded needle-equipped syringe 10 does not employ an adhesive process as a method for holding the injection needle 11 by the barrel 12. Therefore, there is no possibility that the medicine has contact with an adhesive having a negative effect. Also, even when the injection molding die 20 has a simple structure and can be easily and inexpensively formed, the inclination of the injection needle 11 can be prevented. Therefore, the needle-equipped syringe 10 can be inexpensively manufactured, while efficiencies of the process of injection molding and the process for inserting a cap into the injection needle 11 can be improved. Since the flow lines of the syringe and the injection needle 11 to the punctured part substantially coincide with each other, it is not necessary to adjust the direction of the syringe according to the inclination of the injection needle 11, and an efficiency and reliability of the medical practice such as the puncture can be improved. In addition, the inclination of the injection needle 11 and generation of the defective molding such as a weld line and a flow mark are reduced. Therefore an anxious patient will not be agitated by the injection needle 11 falling out of the barrel 12, by difficulties removing the injection needle 11 from the surface of the body after the injection, or by apprehension that impurities are mixed into the medicine.

The direction in which the core pin 21b is eccentric (i.e., offset) is not the direction of the resin injection gate 28, and may be the direction of the inclination of the injection needle 11 when the pressure and the speed of the resin filled into the cavity space become substantially uniform around the core pin 21b in the axis direction of the core pin 21b.

A distance in which the core pin 21b is eccentric (i.e., offset) is different according to the maximum filling amount of the medicine of the needle-equipped syringe 10 because the length and thickness of the core pin 21b, the material thickness of the body 14 of the molded article, and the resin to be used are different according to the maximum filling amount to be required. When the maximum amount of filled medicine of the needle-equipped syringe 10 is one mL, a difference between the thicknesses of the thick part 14b and the thin part 14a at the proximal end part of the body 14 of the barrel 12 is of 80 to 120 μm. When the difference is within the range, the injection needle 11 is prevented from being inclined to the side of the resin injection gate 28. On the other hand, when the difference exceeds the range, the injection needle 11 is excessively inclined to the side opposite to the resin injection gate 28.

When the barrel 12 to be molded is long and narrow, the core pin 21b accordingly becomes long and narrow. Therefore, the injection needle 11 is more easily inclined. Therefore, it is preferable that the length of the parts for forming the inner peripheral surfaces of the body 14 of the barrel 12 of the core pin 21b and the opening part 16 in the axis direction be four to twelve times a diameter of the proximal end of a part where the cavity space of the core pin 21b is formed. Especially, when the maximum filling amount of the medicine is one mL, it is preferable that the length be seven to nine times the diameter. When the length exceeds this ranges, inclination of the injection needle 11 cannot be sufficiently reduced.

Also, in the molded needle-equipped syringe 10, it is preferable that the length from the distal end of the body 14 to the proximal end of the opening part 16 in the axis direction of the body 14 be four to twelve times the internal diameter of the proximal end of the body 14. Especially, when the maximum filling amount of the medicine is one mL, it is preferable that the length be seven to nine times the internal diameter.

An example in which the flange 16a is molded has been illustrated. However, it is not necessary to mold the flange 16a.

Figure 4:
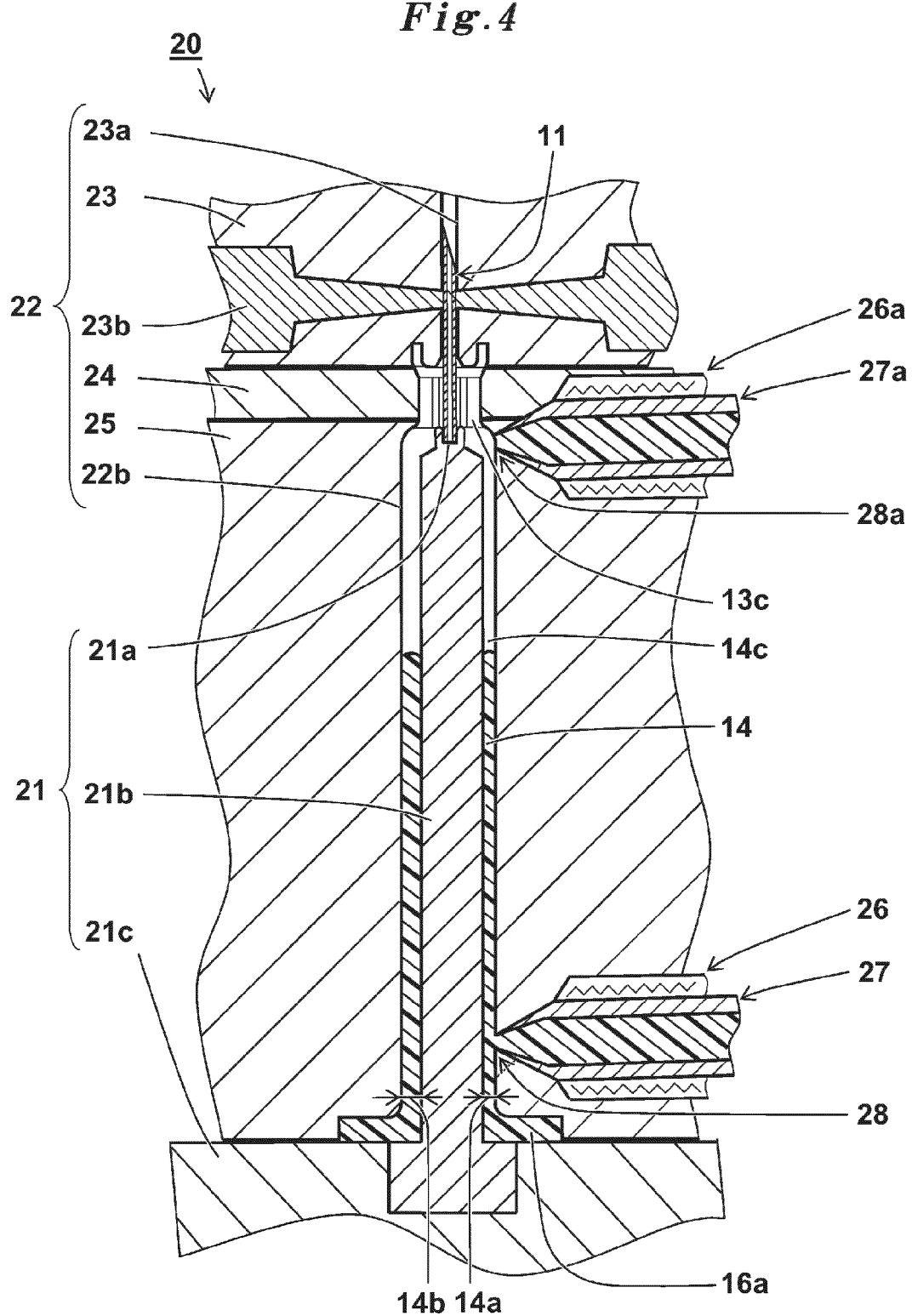
FIG. 4 is a schematic cross-sectional diagram of a state where the resin is injected into another injection molding die when the needle-equipped syringe according to an embodiment of the present invention is manufactured.

As illustrated in FIG. 4, the resin injection gate 28 and the runner 27 may communicate with the cavity space on the side surface of the body 14 of the barrel 12 to which the resin is filled. Also, a resin injection gate 28a and a runner 27a may communicate with the cavity space of a shoulder part where the resin is filled. A plurality of resin injection gates 28a and runners 27a may be provided. A heater 26a may be provided around the runner 27a. In addition, the resin injection gate 28 and the runner 27 may be provided in the male die 21.

In the fitting plate 21c, when the female die 24 is placed on the male die 21, an unevenness may be formed in a part where the cavity space is formed. After the needle-equipped syringe 10 has been molded and taken out, the fitting plate 21c may be integrated with the core pin 21b in a separable manner.

In the female die 22, the nozzle part forming female die 24 may be integrated with the body forming female die 25 or the needle holding female die 23. Also, the body forming female die 25, the nozzle part forming female die 24, and the needle holding female die 23 may be integrated.

An example has been described in which the holding part 23b is used. However, it is not necessary to use the holding part 23b.

The cold runner may be used for the injection molding die 20 instead of the hot runner.

Embodiment

An example for forming a needle-equipped syringe 10 by using an injection molding die 20 to which certain embodiments of the present invention is applied will be described.

Insert molding is performed for a 27-gauge stainless injection needle 11 with cycloolefin polymer which is thermoplastic resin by using an injection molding die 20 according to the embodiment of the present invention illustrated in FIG. 2. A needle-equipped syringe 10 is manufactured which has a barrel 12 having a total length (i.e., a length from the distal end of a nozzle part 13 to the proximal end of an opening part 16) of 64.5 mm, an external diameter of 8.1 mm, and an internal diameter of 6.3 mm. An embodiment of the present invention is an example in which the needle-equipped syringe 10 is formed by arranging a core pin 21b as being close to a resin injection gate 28 by 45 μm from an axis of a recessed part 22b in a cavity space. A comparative example is an example in which the needle-equipped syringe 10 is formed by arranging the core pin 21b so as to substantially coincide with the axis of the recessed part 22b in the cavity space. Regarding the obtained needle-equipped syringe 10, the thicknesses in four directions of a body 14 of the barrel 12 are measured at the proximal end part of the body 14. Also, the angle of the inclination of the needle-equipped syringe 10 from the axis direction of the barrel 12 to the side of a thin part 14a or the side of a thick part 14b is measured. The results are illustrated in Table 1 below.

TABLE 1

| n = 4 | Thickness measured value (mm) | | | | Injection needle inclination (°) |
| --- | --- | --- | --- | --- | --- |
| | Side of gate mark (right side in FIG. 2) | Front side of gate mark (surface side in FIG. 2) | Opposite side of gate mark (left side of FIG. 2) | Deep side of gate mark (rear surface side in FIG. 2) | |
| Embodiment | 0.95 (thin part) | 1.00 | 1.04 (thick part) | 0.98 | 1.5 |
| | 0.96 (thin part) | 1.01 | 1.06 (thick part) | 1.00 | 0.8 |
| | 0.95 (thin part) | 1.00 | 1.04 (thick part) | 0.98 | 1.2 |
| | 0.96 (thin part) | 1.01 | 1.06 (thick part) | 1.00 | 1.8 |
| Comparative example | 1.02 | 1.03 | 1.01 | 1.00 | 2.5 |
| | 1.01 | 1.00 | 0.99 | 1.01 | 4.1 |
| | 1.02 | 1.01 | 0.99 | 1.00 | 3.7 |
| | 1.01 | 0.99 | 0.98 | 1.00 | 3.2 |

As seen in Table 1, in the needle-equipped syringe 10 according to an embodiment of the present invention, the inclination of the injection needle 11 is 0.8 to 1.8°. It is not necessary for a doctor or a nurse to adjust the inclination of the injection needle 11. On the other hand, regarding the needle-equipped syringe of the comparative example, the inclination of the injection needle is of 2.5 to 4.1°. Therefore, there is a possibility that a target cannot be punctured as intended.

By molding the needle-equipped syringe according to certain embodiments of the present invention by using the injection molding die, the needle-equipped syringe can be used to improve the efficiency of the medical practice such as the puncture. The injection molding die according to certain embodiments of the present invention can be used to improve the efficiency of the process for inserting the cap into the injection needle and improve the safety of the manufactured needle-equipped syringe. Also, the manufacturing method for the needle-equipped syringe according to certain embodiments of the present invention can be used to improve the efficiency of the process for molding the needle-equipped syringe.

REFERENCE SIGNS LIST 10 needle-equipped syringe
11 injection needle
12 barrel
13 nozzle part
13a cavity space corresponding to part of nozzle part
14 body
14a thin part
14b thick part
14c cavity space corresponding to part of body
15 hollow part
15a peripheral wall
16 opening part
16a flange
17 gate mark
20 injection molding die
21 male die
21a holding hole
21b core pin
21c fitting plate
22 female die
22b recessed part
23 needle holding female die 23a storing hole
23b holding part
24 nozzle part forming female die
25 body forming female die
26, 26a heater
27, 27a runner
28, 28a resin injection gate
$A_1, A_2, A_3$ opening direction
$B_n$ axis of injection needle which is not inclined
$B_I$ axis of inclined injection needle
$C_{I.D.}$ axis of inner peripheral surface
$C_{O.D.}$ axis of outer peripheral surface
$\theta$ inclination of axis of inclined injection needle with respect to axis of injection needle which is not inclined

The invention claimed is:

1. A needle-equipped syringe comprising:
   a barrel formed using a resin and having a cylindrical body, a nozzle part provided at a distal end of the body, and an opening part provided at a proximal end of the body; and
   an injection needle configured to be held by the nozzle part, wherein:
   the injection needle and the barrel are integrally molded so that an axis of the injection needle is substantially parallel to an axis of the body,
   at a proximal end of the body, both an outer surface of the body and an inner surface of the body are entirely curved in a circumferential direction of the body,
   at the proximal end of the body, the body has a thick part and a thin part at positions opposed to each other across the axis of the body, and
   at the proximal end of the body, an axis of the inner surface of the body is offset from an axis of the outer surface of the body.

2. The needle-equipped syringe according to claim 1, wherein a length from the distal end of the body to the proximal end of the body in the axis direction of the body is four to twelve times an internal diameter of the proximal end of the body.

3. The needle-equipped syringe according to claim 1, wherein a difference between a thickness of the thick part and a thickness of the thin part is 50 to 500 μm.

4. The needle-equipped syringe according to claim 1, wherein an inclination of the axis of the injection needle with respect to the axis of the body is equal to or less than 2°.

5. The needle-equipped syringe according to claim 1, wherein a single gate mark generated at a time of molding the barrel is provided on the opening part of the barrel or the outer surface of the body, and the thin part is provided at a side of the gate mark in the circumferential direction of the body.

6. The needle-equipped syringe according to claim 5, wherein:
   the opening part includes a flange extending perpendicularly to the axis of the body, and
   the single gate mark is provided on an outer surface of the flange.

* * * * *